United States Patent [19]

Price

[11] 4,022,202
[45] May 10, 1977

[54] RESUSCITATOR INHALATOR OXYGEN VENTILATOR

[76] Inventor: William Edward Price, 5 Franklin Avenue, West Hill, Ontario, Canada

[22] Filed: Oct. 22, 1975

[21] Appl. No.: 624,991

[30] Foreign Application Priority Data

Jan. 17, 1975   Canada .............................. 218069

[52] U.S. Cl. ............................. 128/145.8; 128/210
[51] Int. Cl.² ...................................... A61M 16/00
[58] Field of Search ......... 128/145.8, 145.5, 142 R, 128/209, 210, 208

[56] References Cited

UNITED STATES PATENTS

| | | | |
|---|---|---|---|
| 2,897,833 | 8/1959 | Seeler ............................ | 128/145.8 |
| 3,717,147 | 2/1973 | Flynn ............................ | 128/145.8 |
| 3,850,171 | 11/1974 | Ball et al. ..................... | 128/145.8 |
| 3,853,105 | 12/1974 | Kenagy ......................... | 128/145.8 |
| 3,874,378 | 4/1975 | Isaacson et al. ............... | 128/145.8 |

Primary Examiner—Robert W. Michell
Assistant Examiner—Henry J. Recla

[57] ABSTRACT

A resuscitator inhalator device for the administration of oxygen or mixtures of oxygen and air to a striken person is disclosed. The device consists of a body connected to a supply of oxygen under pressure. The body has a manually operated valve permitting flow of oxygen under pressure through the body to the person and which permits continuous flow of oxygen or for manually operated intermittent flow. A metered orifice is provided within the body for metering a maximum pressure of oxygen which can pass therethrough to a patient. A supplementary metering arrangement is selectively adjustable to permit increased pressure flow of oxygen to the patient, the highest possible pressure of oxygen which can pass through the device to the patient being not greater than the highest safe pressure for a healthy lung. An adjustment ring on the body permits the device to administer pure oxygen or a mixture of oxygen and air.

9 Claims, 9 Drawing Figures

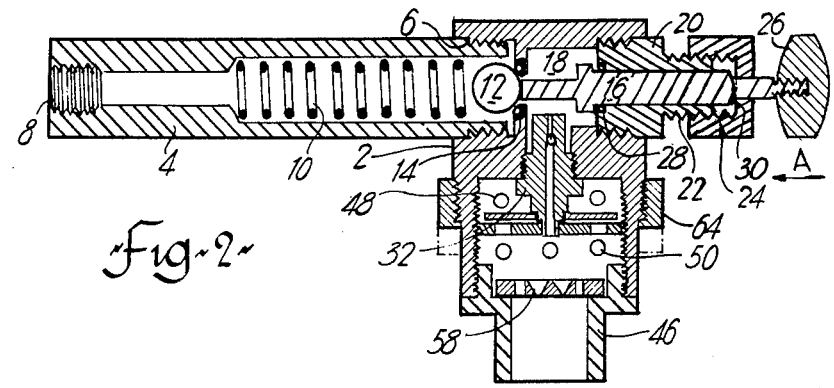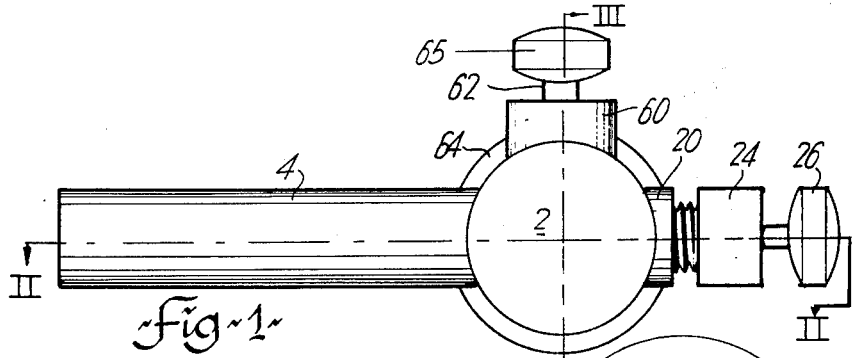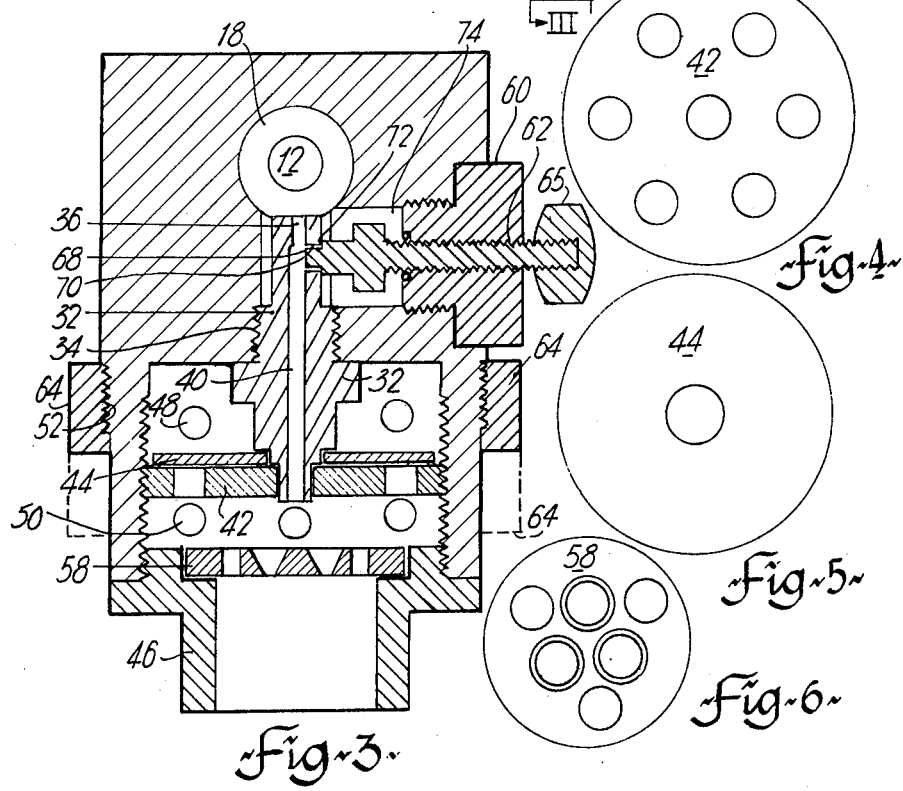

RESUSCITATOR INHALATOR OXYGEN VENTILATOR

A resuscitator inhalator ventilator device for use with a source of oxygen and with a standard tight-fitting face piece is described.

The ventilator device may be used selectively as a resuscitator or as an inhalator with pure oxygen or mixtures of oxygen and air for both inhalation and resuscitation.

The device provided for manually dispensed intermittent doses of pure oxygen at selected minimum, intermediate, and maximum pressures, thus positively avoiding pressures of a degree which would cause lung damage; and which is selectively adjustable whereby a continuous flow of oxygen at selected minimum intermediate and maximum pressures can be administered, thus enabling the device to be used in toxic or poisonous atmospheres to revive or sustain a patient; and which is selectively adjustable for use as an inhalator providing for supply of pressurized oxygen pure or in mixture with air when the device is to be used as an inhalator.

The primary object of the invention is to provide a ventilator device which is adapted for use selectively as a resuscitator or as an inhalator with pure oxygen or mixtures of oxygen and air for both inhalation and resuscitation.

A specific object of the invention is to provide a resuscitator inhalator ventilator device for use with a supply of oxygen under pressure for administering to a patient comprising, a body, and conduit means connecting the body to a supply of oxygen under pressure, and a manually operated primary valve permitting flow of oxygen under pressure through the conduit means and into the body, and means for selectively controlling the primary valve for continuous flow of oxygen or for manually operated intermittent flow, and a metered orifice within the body metering a maximum pressure of oxygen which can pass therethrough to a patient, and supplementary metering means selectively adjustable to permit increased pressure flow of oxygen to the patient, the highest possible pressure of oxygen which can pass through the device to the patient being not greater than the highest safe pressure for a healthy lung, and adjustment means on the body permitting the device to administer pure oxygen or a mixture of oxygen and air.

Resuscitator and inhalator apparatus presently in use and known to applicant all employ a diaphragm arrangement to control the pressure of oxygen delivered to a patient. Diaphragms by their very nature are susceptible to rupture from time to time and the increased pressure of oxygen being supplied to the victim may cause serious lung damage. The present device does not employ a diaphragm for pressure control, but rather uses specifically metered orifices thus positively ensuring at all times that the passage of pressure harmful to the lungs of a patient is avoided.

The device is primarily intended for manual operation for supplying oxygen to a patient under emergency conditions. Many of the devices known to applicant will supply only a mixture of air and oxygen, whereas the present device may selectively be regulated to provide either pure oxygen or a mixture of oxygen and air, and in the former case, the device is particularly well adapted for use in toxic and poisonous atmospheres. This provision enables a rescue crew to start treatment as soon as the patient has been reached.

As such devices are primarily used by non-medical personnel, e.g., fire fighters, police, and ambulance personnel, under conditions where no case history is available, safeguards have been built into the present unit. An initial low pressure flow is available at 17 cm of water (5 oz.) that is safe for a diseased lung. If higher pressures are required to ventilate the patient, they are available at 34 cm of water (10 oz.) second stage, and 51 cm (15 oz.) third stage, which is the highest safe pressure for a healthy lung, and the present device is so constructed that the device will not exceed this safe maximum pressure.

The present invention will now be more fully described with reference to the accompanying drawings wherein:

FIG. 1 illustrates in top view the ventilator device according to one embodiment of the present invention;

FIG. 2 is a view taken along line 2—2 of FIG. 1;

FIG. 3 is a sectional view taken along line III—III;

Figure 8:
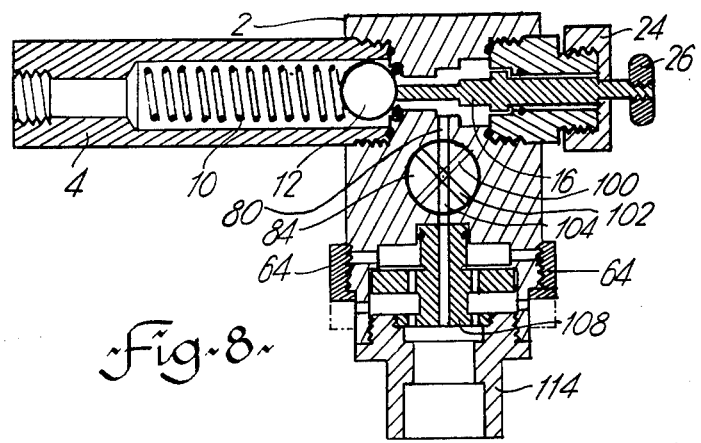
Figure 7:
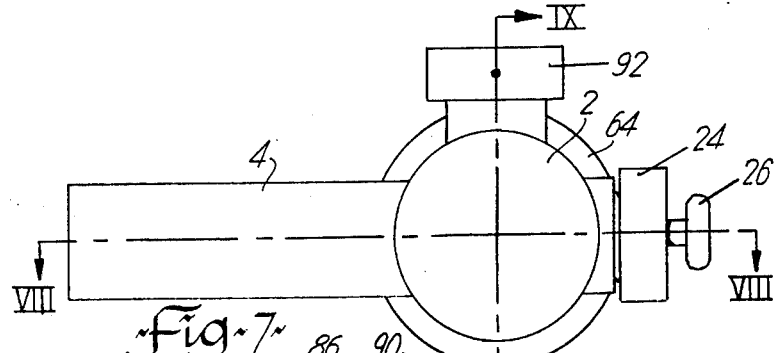

FIGS. 4, 5, and 6 are enlarged plan views of component parts of the device;

FIG. 7 illustrates a second embodiment of the invention in top view;

FIG. 8 is a sectional view along lines VIII—VIII of FIG. 7; and

Figure 9:
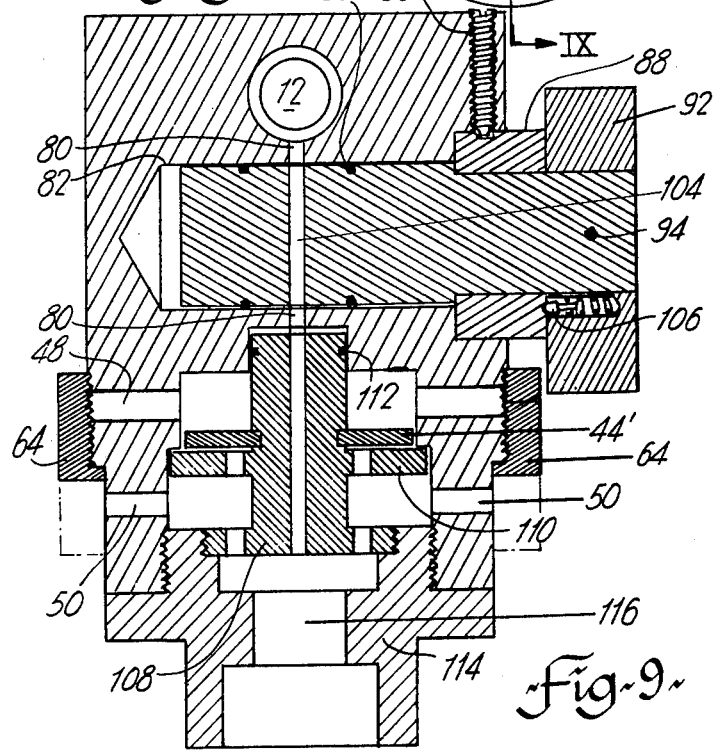

FIG. 9 is a sectional view taken along lines IX—IX of FIG. 7.

Reference will now be had to the accompanying drawings wherein like numerals refer to like parts.

The ventilator valve arrangement consists of a body 2 to which is secured a connection conduit 4 by suitable means such as by threading shown at 6. The outer end of the connection conduit 4 is provided with threading 8 for suitable connection to an oxygen supply cylinder (not shown) which includes valve regulator means permitting passage of oxygen to the device at a pressure in the order of 50 lbs. p.s.i. The connection conduit 4 is provided with primary valve means consisting of spring means 10 which hold valve ball 12 snugly against a valve seat consisting of, for example, an O-ring 14. A valve shaft 16 mounted for longitudinal movement to move ball valve 12 from seat 14 to permit entry of oxygen into cavity 18 of body 2 of the device is slidably supported by collar 20 which is threadedly secured to body 2 by means of threading as shown in FIG. 2. The outer end of collar 20 is provided with threading as shown at 22 to receive cap 24. A portion of the shaft 16 projects through an aperture provided in cap 24, and is provided with a trigger knob 26. The shaft 16 is sealingly carried by collar 20 by suitable means such as O-ring 28.

From FIG. 2, it will be clearly appreciated that when ball valve 12 is to be opened, inward movement of trigger button 26 in the direction shown by arrow A will result in a displacement of the ball 12 from seat 14 against the action of spring 10 permitting oxygen under a pressure of about 50 lbs. p.s.i. to enter cavity 18. With a release of inward pressure on knob 26, spring 10 returns ball 12 and the shaft 14 to the position shown in FIG. 2 stopping passage of oxygen. Thus, to enable oxygen under pressure to pass through the device to a resuscitator mask (not shown) applied over the face of a striken individual to permit entry of oxygen into the lungs of the patient and expand the lungs, selected manual inward pressure on knob 26 is applied.

When, however, the present device is to be used as an inhalator and to supply a constant flow of oxygen to the patient, this is accomplished simply by screwing cap 24 inwardly. The shaft 16 is, as shown in FIG. 2, provided with a shoulder or abutment 30 which has a larger diameter than the aperture provided in cap 24, so that when cap 24 is threaded inwardly the cap contacts and moves shaft 16 to the left as shown in FIG. 1, and against ball valve 12 and against the action of spring 10. To cease flow, the cap 24 is simply rotated in the opposite direction to cause it to move outwardly whereby spring 10 returns ball valve 12 to its seated position.

The portions of the ventilation device shown in the lower portion of FIG. 2 are shown in more detailed and enlarged view in FIG. 3.

A metering piece or insert 32 is threadedly received within a cavity (not numbered) provided within body 2 and is held therein by means of suitable threading 34. The upper portion of the metering piece 32 is provided with a calibrated and metered bore 36 of a diameter to reduce the pressure of oxygen passing therethrough from 50 lbs. p.s.i. within cavity 18 to a pressure of 17 cm of water (5 oz.).

Below metered orifice 36 the diameter of a longitudinal bore 40 provided in the metering piece 32 increases as shown for purposes which will be described in more detail hereinafter.

The lower portion of the body 2 is provided as an interiorly threaded cavity (not numbered) to receive an apertured retention washer 42 (FIG. 4) which carries a circular flap valve 44 (FIG. 5), and which is threaded into position within the cavity and around the lower tip of the metering piece 42. The body 2 is then provided with a threaded sleeve projection 46 adapted to receive a standard face mask. The walls of body 2 are provided with sets of apertures 48 above the flap valve 44 and apertures 50 below the flap valve. The exterior of the valve body 2 is provided with suitable threading 52, for reception of an adjustment ring 64. In the position shown in FIG. 3, the apertures 48 are completely covered by the ring 64 whereby preventing passage of any oxygen or air therethrough. By means of threading 52, the adjustment ring 64 may be threaded downwardly to open holes 48 and close holes 50. The position of the adjustment ring 64 in the latter position is shown by broken lines in FIGS. 2 and 3.

The positioning of the adjustment ring in the position shown in full lines in FIGS. 2 and 3 enables the ventilator device to be used to provide a mixture of air and oxygen to the patient with air combining with the oxygen by in-flow through holes 50. When the patient exhales, exhaled air passes outwardly through holes 50.

The positioning of adjustment ring in the position shown in broken lines in FIGS. 2 and 3 covering holes 50 and opening holes 48 enables the device to administer 100% oxygen to the patient, and can as discussed above be used in toxic or poisonous atmospheres without risk to the patient. In this position, exhaled air passes flap valve 44 and outwardly through holes 48.

A description when the device is to be used as a resuscitator (administration of pure oxygen) and means for introducing oxygen under pressure into the lung cavity of a patient during efforts to initiate breathing of the patient will now be provided.

When the device is used as a resuscitator, it is of importance that the pressure of the oxygen introduced into the lung cavity of the patient not be higher than 17 cm of water (5 oz. of pressure) which is the considered safe pressure for a person with a diseased lung. In most instances, rescuers are not aware of the state of health of the lungs of the person they are attempting to revive and to ensure against damage caused by overpressure to a diseased lung, the maximum safe oxygen pressure which can be introduced into the lung cavity should not be more than 17 cm of water. In cases where the condition of the lungs can be determined, it is possible to utilize increased pressures, but as this is very seldom known in emergency cases, the safe approach is to utilize 17 cm of water as maximum pressure.

With the adjustment ring 64 in the position shown in broken lines in both FIGS. 2 and 3, i.e., covering holes 50, with holes 48 being open to ambient air, the device is ready for operation as a resuscitator device whereby spurts or periods of oxygen injection can be provided to a patient by periodically pushing trigger knob 26 inwardly in the direction of arrow A. When this is done, oxygen passes from the cylinder (not shown) through connection conduit 4 and into cavity 18, and through metered orifice 36 and through bore 40 and into and through the hollow sleeve projection 46, and into a resuscitator mask (not shown) and hence into the lungs of the patient. Even though holes 48 are open to ambient air, flap or check valve 44 prevents inflow of ambient air into the device. It has been found that the passage of oxygen outwardly through openings 48 cannot be detected. A vacuum is created, and air may flow in, but not out, until the lung is full.

In order to divide the flow of air evenly through sleeve 46 and into the resuscitator mask, a flow spreader ring 58 (FIG. 6) can be utilized. However, it has been found that such a flow spreader is not absolutely necessary.

When used as a resuscitator the various elements are in a position with the adjustment ring 64 covering holes 50, and by inward pressure on knob 26, a flow of oxygen at 17 cm per water passes through the device through the resuscitator mask and into the lungs of the patient. The operator of the device, once expansion of the lung cavity has occurred, then releases knob 26, and the patient's chest muscles relax to depress the chest cavity to expel air and oxygen which passes outwardly from the device through apertures 48. Once the chest cavity has depressed due to the action of the chest muscles, knob 26 is again pushed to provide a further supply of oxygen to the patient. This procedure is continued until the patient continues a normal breathing pattern.

The above described procedure can be used when the patient and rescuer are in the presence of a toxic or poisonous atmosphere, such as in a burning building.

In the embodiment illustrated in FIGS. 2 and 3, the body 2 is additionally provided with supplementary metering means consisting of a threaded plug 60 which itself threadedly carries a valve stem 62. The valve stem 62 moves inwardly and outwardly with respect to the plug 60 and the body 2 as a result of rotation of knob 65. The inner end of the valve stem 62 is provided as a needle plug 68 or the like which engages into a lateral metered bore 70 in communication with bore 40 below metered orifice 36. Seating is accomplished by contact of shoulder 72 with the side of the metering piece 32 around bore 70.

When the shoulder 72 tightly covers bore 70, the only oxygen which can pass through the metering piece 32 is that which passes through the metered orifice 36. When, however, the shoulder 72 is removed from tight seating within hole 70, an additional supply of oxygen can flow to the patient. The hole 70 is in communication with cavity 74 which is open with cavity 18 so that when valve stem 62 is opened, oxygen under pressure will flow through metered bore 36, and also hole 70.

By opening (by turning) knob 65, shoulder 72 is removed from tight contact with the metering piece permitting passage of oxygen under pressure therethrough. By turning knob 65 a small amount (perhaps a ½ turn) the plug 68 still is present within hole 70; the latter having a larger diameter than the plug 68. While oxygen can flow through the hole 70, full flow is prevented by the presence of plug 68. This is a second stage of pressurization which is a combination of flow through metered orifice 36 and partially plugged hole 70, and provides a pressure of oxygen to the patient of 34 cm of water (10 oz.).

By fully opening knob 65, plug 68 becomes completely removed from within hole 70, and full flow therethrough is possible. The size of the hole 70 is so calibrated that the pressure of oxygen flow therethrough plus the pressure of oxygen flow through metered orifice 36 provided an oxygen pressure flow at 51 cm of water to the patient at this third stage of pressurization, which is the maximum safe pressure for a healthy lung. The latter is a third stage of pressurization.

When the device is used to administer 100% pure oxygen, the adjustment ring 64 is in its lower threaded position covering holes 50, and in this position of the adjustment ring 64 and the holes 48 are open to ambient atmosphere. If the patient is unconscious automatic contraction of the chest muscles expels air from the lungs, and this expelled air passes from the device by passing valve 44 and outwardly through openings 48. If the patient is conscious and breathing regularly, air expelled by the patient also exists through holes 44. With an arrangement of the device with the adjustment ring 64 covering holes 50, the structure can be used in a toxic atmosphere with no toxic air entering the patient's lungs when the face mask is held tight against the patient's face.

However, when it is desired to treat the patient by the application of a combination of oxygen and air, the adjustment ring 64 is raised to its threaded upward position, thus opening holes 50 and closing holes 48.

When the device is used as in inhalator and the patient is breathing more or less normally and when a mixture of air and oxygen is desired, the adjustment ring 64 is positioned in its uppermost position covering holes 48 so that the patient receives both oxygen and air entering the device through the holes 50.

A majority of parts of the device shown in FIGS. 7, 8, and 9 are identical with portions of the embodiment shown in FIGS. 1 through 6 inclusive, and identical reference numerals are used.

The basic differences in the embodiment shown in FIGS. 7, 8, and 9 involve a metering piece assembly for providing a patient with a minimum pressure of oxygen and means for adjusting the pressure of oxygen supply between minimum, intermediate, and maximum pressures; and the specific arrangement of the lower portion of the device which provides for facilitated cleaning of the apparatus.

Very often, a striken person when being revised becomes sick to his stomach, and as the facepiece is held tightly over the mouth and nose of the patient, a sudden sickness will result in dirtying of the device and possible clogging or malfunction of important components.

With reference now to FIGS. 8 and 9, it will be seen that the body 2 of the device is provided with a straight through bore shown at 80 with the bore being so metered and calibrated that the maximum pressure of oxygen which can pass through the body 2 to the patient is 51 cm of water, which is the safe maximum pressure for a healthy lung. Intersecting bore 80 at right angles a further bore or circular opening 82 is provided, to receive a cylindrical plug 84 which is rotatably carried therein. The plug 84 is provided with sealing means such as O-rings 86 to prevent leakage as will be understood from the following description. A collar 88 is provided around the plug 84 and is received within a recess (not numbered) provided in body 2 and may be held suitably therein by means of set screw 90.

The outer end of the plug 84 is provided with a knob 92 so that manual rotation of the plug 84 may be effected. The knob 92 may be held integral with plug 84 by any suitable means such as pin 94.

The plug 84 is provided with three intersecting metered orifices arranged suitably at an angle of 60° with respect to each other as clearly shown in FIG. 8. The first and smallest of the metered orifices 100 has a bore calibrated to a size identical with the size of metered orifice 36 of the foregoing disclosure, and it will be appreciated that when knob 92 is rotated so that metered orifice 100 is in alignment with bore 80, that the maximum pressure that can pass therethrough and to the patient will be the maximum safe pressure to be administered to a person having a diseased lung, and of the order of 17 cm of water as indicated in the foregoing disclosure.

A second or larger 104 of the metered orifices has a calibrated and metered bore enabling the passage therethrough of a pressure of 51 cm of water which as indicated earlier is the safe maximum pressure for a person having a healthy lung.

A third or intermediate sized orifice 102 has a calibrated diameter enabling the passage therethrough of a pressure or oxygen in the order of 34 cm of water.

As a result, it will be appreciated by selective rotation of 92 and hence plug 84, that selected pressures of oxygen in amounts of 15, 34, and 51 cms of water can be administered to the patient. To enable the user of the device to positively determine the exact pressure of oxygen being delivered to the patient, the knob 92 may be provided with a spring-loaded plunger 106 which will positively engage in recesses (not numbered) provided in collar 88 and arranged at 60° intervals so that after rotation of the handle 92, the selected pressure orifice is "locked" in position. Of course, the handle 92 or the collar 88 or the body 2 itself may be suitably inscribed or marked to enable the person operating the device to know what pressure is being administered to the patient.

Below the plug 84 and in alignment with bore 80 is an insert piece 108 which is integral with a perforated support plate 110 which carries a circular valve washer 44' performing in the same manner as indicated above. The upper end of the insert piece 108 may advantageously be provided with an O-ring 112 for sealing engagement with the body 2. The insert piece 108 is held in position by threading engagement with a projecting sleeve 114 the lower cylindrical portion of which is adapted for securement to a standard face mask.

The positioning and function of the apertures of the sets of openings 49 and 50 and the adjustment ring 64 are as described in the foregoing disclosure.

In the embodiment shown in FIGS. 7, 8, and 9, a flow spreading ring is not necessary, but it has been found that the provision of a constricted portion 116 in the sleeve 114 is necessary so that air passing downwardly through the aligned bores is directly supplied to the patient. As oxygen passes through the construction 116, it has been found that with the adjustment ring 64 in the position shown in full lines in FIG. 9, that a Venturi effect takes place to draw air inwardly through apertures 50 whereby supplying a mixture of oxygen and air to the patient.

From the detail given in FIG. 9, it will be appreciated that the apparatus of this embodiment may very quickly and easily be disassembled for cleaning. To effect cleaning the sleeve 114 is simply unthreaded from the bottom of the body 2 and this results also in removing insert piece 108 and the valve arrangement 44' from the body. In the event that cleaning of the metered orifices 100, 102 and 104 provided in plug 84 also is necessary, the removal of the plug is easily accomplished by simply loosening set screw 90 and withdrawing the plug.

I claim:

1. A resuscitator inhalator ventilator device for use with a supply of oxygen under pressure for administering to a patient comprising;

a body including a first passageway extending therethrough, and means for connecting one end of said first passageway to a supply of oxygen under pressure, and a hollow projecting sleeve secured to the body and communicating with the other end of said first passageway and adapted for securement to a face mask, and a manually operated primary valve in said first passageway controlling the flow of oxygen under pressure to the face mask, and means for selectively controlling the primary valve for continuous flow of oxygen or for manually operated intermittent flow, and a metered orifice within said first passageway downstream of said primary valve metering a maximum pressure of oxygen which can pass therethrough to a patient, which maximum pressure being not greater than the highest safe pressure for a healthy lung, and supplementary metering means by passing said metered orifice selectively adjustable to enable administration of oxygen at pressures less than said maximum pressure, a first and second set of openings in side walls of the body and communicating with said first passageway, said second set being longitudinally spaced downstream of said first set, and adjustment means on said body selectively movable from a position covering one set of openings to a position covering the other set and to intermediate positioning partially covering both sets of openings, and a one-way valve positioned transversely in said passageway between the two sets of openings preventing flow in the downstream direction whereby, inward flow of ambient air into the device through said first set of openings is prevented when said second set is covered by the adjustment means while permitting discharge of air through said first set, and the positioning of the adjustment means over the said first set of openings enables inward flow and discharge of air through the second set of openings, a second passageway within said first passageway extending through said oneway valve and communicating said metered orifice and said first passageway downstream of said one-way valve.

2. Device according to claim 1, the means for selectively controlling the primary valve consisting of a valve shaft slidably carried by the body and manually slidable inwardly against spring tension to provide said intermittent flow, and means to hold the valve shaft inwardly against the spring tension to provide the said continuous flow of oxygen.

3. Device according to claim 1, the said adjustment means comprising an adjustment ring threadedly mounted on the body exteriorly thereof and manually rotatable to positions covering the two sets of openings and intermediate positioning partially covering both sets of openings.

4. A device according to claim 1 wherein the metered orifice is a metered bore of a calibrated diameter permitting passage therethrough of oxygen under maximum pressure of 51 cms. of water, the supplementary metering means being in the form of a rotatable plug inersecting the metered bore, the rotatable plug having intersecting metered orifices of varying size extending radially therethrough, rotation of the rotatable plug permitting alignment of selected one of the metered orifices with the said metered bore, a first of the metered orifices having a calibrated diameter permitting passage therethrough of oxygen under maximum pressure of 17 cm. of water.

5. Device according to claim 4, wherein a second of the metered orifices permitting passage of oxygen therethrough under maximum pressure of 51 cms of water.

6. Device according to claim 5, a third of the metered orifices having a diameter of a size permitting passage therethrough of oxygen under maximum pressure of 34 cm of water.

7. A resuscitator inhalator ventilator device for use with a supply of oxygen under pressure for administering to a patient comprising;

a body including a first passageway extending therethrough and means for connecting one end of said first passageway to a supply of oxygen under pressure, and a hollow projecting sleeve secured to the body and communicating with the other end of said first passageway and adapted for securement to a facemask, and a manually operated primary valve in said first passageway controlling the flow of oxygen under pressure to the facemask, and means for selectively controlling the primary valve for continuous flow of oxygen or for manually operated intermittent flow, and a metered bore within said first passageway downstream of said primary valve metering a maximum pressure of oxygen which can pass therethrough to a patient, which maximum pressure being not greater than the highest safe pressure for a healthy lung and being not greater than 51 cm. of water, and supplementary metering means by passing said metered orifice selectively adjustable to enable administration of oxygen at pressures less than said maximum pressure, the supplementary metering means comprising a rotatable plug intersecting the metered bore, the rotatable plug having intersecting metered orifices of varying size extending radially therethrough, rotation of the rotatable plug permitting alignment of selected one of the metered orifices with the said metered bore, a first of the metered orifices having a calibrated diameter permitting passage therethrough of oxygen under maximum pressure of 17 cm. of water, a first and second set of openings in the side walls of the body and communicating with said first passageway, said second set being longitudinally spaced downstream of said first set, and adjustment means on said body selectively movable from a position covering one set of openings to a position covering the other set of openings, and a one-way valve positioned transversely in said passageway between the two sets of openings preventing flow in the downstream direction whereby, inward flow of ambient air into the device through said first set of openings is prevented when said second set is covered by the adjustment means while permitting discharge of air through said first set, and the positioning of the adjustment means over the said first set of openings enables inward flow and discharge of air through the second set of openings, a second passageway within said first passageway extending through said one-way valve and communicating said metered bore with said first passageway downstream of said one-way valve.

8. Device according to claim 7 wherein a second of the metered orifices permitting passage of oxygen therethrough under maximum pressure of 51 cm. of water.

9. Device according to claim 7 wherein a third of the metered orifices permitting passage therethrough of oxygen under maximum pressure of 34 cm. of water.

* * * * *